(12) United States Patent
Yoon (10) Patent No.: US 6,875,167 B2
(45) Date of Patent: Apr. 5, 2005

(54) APPARATUS FOR GENERATING BRAIN WAVE-INDUCING SIGNALS AND NETWORK SYSTEM INCLUDING THE SAME

(75) Inventor: James Yoon, Seoul (KR)

(73) Assignee: DREAMFREE, Inc., Seoul (KR)

( * ) Notice: Subject to any disclaimer, the term of this patent is extended or adjusted under 35 U.S.C. 154(b) by 288 days.

(21) Appl. No.: 10/186,998

(22) Filed: Jul. 2, 2002

(65) Prior Publication Data

US 2003/0195383 A1 Oct. 16, 2003

(30) Foreign Application Priority Data

| Apr. 12, 2002 | (KR) | 2002-11116 |
| Apr. 12, 2002 | (KR) | 2002-20148 |
| Apr. 12, 2002 | (KR) | 2002-20149 |
| Apr. 12, 2002 | (KR) | 2002-20152 |

(51) Int. Cl.$^7$ .......................................... A61M 21/00
(52) U.S. Cl. ................................................... 600/27
(58) Field of Search ........................ 600/26, 27, 28, 600/545

(56) References Cited

U.S. PATENT DOCUMENTS

| 5,036,858 A | * | 8/1991 | Carter et al. ............. 600/27 |
| 5,219,322 A | * | 6/1993 | Weathers ................. 600/27 |
| 5,304,112 A | * | 4/1994 | Mrklas et al. ............ 600/27 |
| 5,306,228 A | * | 4/1994 | Rubins .................... 600/27 |
| 5,409,445 A | * | 4/1995 | Rubins .................... 600/27 |
| 6,071,229 A | * | 6/2000 | Rubins .................... 600/27 |
| 6,264,614 B1 | * | 7/2001 | Albert et al. ............. 128/904 |
| 6,299,632 B1 | * | 10/2001 | Jaillet .................... 600/27 |
| 6,406,426 B1 | * | 6/2002 | Reuss et al. ............. 600/300 |

* cited by examiner

Primary Examiner—Eric F. Winakur
(74) Attorney, Agent, or Firm—Antonelli, Terry, Stout & Kraus, LLP (57) ABSTRACT

An apparatus is disclosed for generating brain wave-inducing signals and a network system including the same. The apparatus for generating brain wave-inducing signals has a system controller, a data input/output port and a brain wave-inducing signal generating unit. The data input/output port receives digital signals from an external device. The brain wave-inducing signal generating unit generates an audio signal and a light emission signal under the control of the system controller. The present invention is advantageous in that it can be miniaturized by integrating several parts into one through the combination of simple hardware with software, and can receive analog and digital signals from an external device. Further, the present invention is advantageous in that it can increase the variety of signal selection by downloading a suitable brain wave-inducing signal according to the characteristics of users from an external communication network.

26 Claims, 12 Drawing Sheets

```
[VER]1.0
[SNO]re0001
[NAM]Relaxation-15-N
[M01]300,5,0,0,7,11110000,540,1080
[M02]360,5,0,0,7,11110000,1080,1080
[M03]240,5,0,0,7,10100101,1080,415
[DES]This is a mode required for rest,
     which helps your body be easy if
     you use this mode when you feel
     excitement or fatigue.

Signal Characteristic
Time: 15 Minutes, Pitch: N
```

APPARATUS FOR GENERATING BRAIN WAVE-INDUCING SIGNALS AND NETWORK SYSTEM INCLUDING THE SAME

BACKGROUND OF THE INVENTION

1. Field of the Invention

The present invention relates generally to an apparatus for generating brain wave-inducing signals, and more particularly to an apparatus for generating brain wave-inducing signals and network system including the same, which can be miniaturized by integrating several parts into one through combination of simple hardware with software, can receive analog and digital signals from an external device, and can increase the variety of signal selection by downloading a suitable brain wave-inducing signal according to characteristics of users through an external communication network.

2. Description of the Prior Art

Generally, currents are generated while human brain cells process information received from sense organs (eyes, ears, nose, mouth and skin). Brain waves are electrical waves obtained by deriving, amplifying and recording such currents. The types of electrical waves emitted from the brain vary according to brain activities, which are complicated information processing procedures. The electrical wave types are classified into alpha, beta, delta and theta waves according to their frequencies.

In general, the alpha waves, with frequencies of 8 to 13 Hz, are generated under stable conditions of a normal person, such as during paying attention, simple learning, meditation, etc. The beta waves, with frequencies of 14 to 30 Hz, are generated in states of increased brain activity, or when working under strain. The theta waves, with frequencies of 4 to 7 Hz, are generated during light sleep. The delta waves, with frequencies of lower than 4 Hz, are generated during deep sleep, and are independently generated by an external cortex itself.

Brain wave frequencies of a human brain tend to correspond to or be resonant with frequencies of external stimulation, which tendency is so-called a frequency following response (FFR). A brain wave-inducing signal is a signal formed to induce specific brain waves using the above FFR principle. Most brain wave-inducing signals use light and sound as stimulation. An optical glasses unit in which light emitting diodes (LEDs) are mounted is used to provide light stimulation, while an earphone is used to provide sound stimulation.

Conventional apparatuses for generating brain wave-inducing signals are each comprised of a main body, an optical glasses unit and an earphone, or comprised of a personal computer and an optical glasses unit. Conventional apparatuses comprised of a main body and an optical glasses unit cannot use other brain wave-inducing signals, except for the originally installed brain wave-inducing signals provided by the apparatuses themselves. Therefore, the above apparatuses are problematic in that, since a limited number of signals can be originally provided, it takes much time for a user to become accustomed to a brain wave-inducing signal, or the user fails to adapt to a brain wave-inducing signal, so the apparatuses are almost ineffective. This phenomenon is due to a fact that brain wave characteristics of individual users are different, and degrees of responses of individual users to the brain wave-inducing signals are also different.

Further, in order to overcome the above problems, there is designed an apparatus, in which an optical glasses unit is connected to a personal computer and used, so as to simplify the construction of a brain wave-inducing signal generating apparatus and provide various brain wave-inducing signals to a user. However, the apparatus is problematic in that, if the personal computer cannot be used, the brain wave-inducing signal generating apparatus also cannot be used.

SUMMARY OF THE INVENTION

Accordingly, the present invention has been made keeping in mind the above problems occurring in the prior art, and an object of the present invention is to provide an apparatus for generating brain wave-inducing signals, which can be miniaturized by integrating several parts into one through combination of simple hardware with software, can receive analog and digital signals from an external device, and can increase the variety of signal selection by downloading a suitable brain wave-inducing signal according to characteristics of users through an external communication network.

Another object of the present invention is to provide a method of downloading a brain wave-inducing signal file, and a network system, which can download a brain wave-inducing signal file of a desired mode from a Web server on a network using a brain wave-inducing signal generating apparatus having a predetermined communication program so as to be communicatable with a client having a browser.

In accordance with one aspect of the present invention, the above and other objects can be accomplished by the provision of an apparatus for generating brain wave-inducing signals, comprising a system controller; a data input/output port for receiving digital signals from an external device; and a brain wave-inducing signal generating unit for generating an audio signal and a light emission signal under the control of the system controller.

In accordance with another aspect of the present invention, there is provided an apparatus for generating brain wave-inducing signals, comprising a system controller; a data input/output port comprised of a single port for receiving analog and digital signals from the outside; signal separating means for separating the analog signals and digital signals; and a brain wave-inducing signal generating unit for generating an audio signal and a light emission signal under the control of the system controller.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
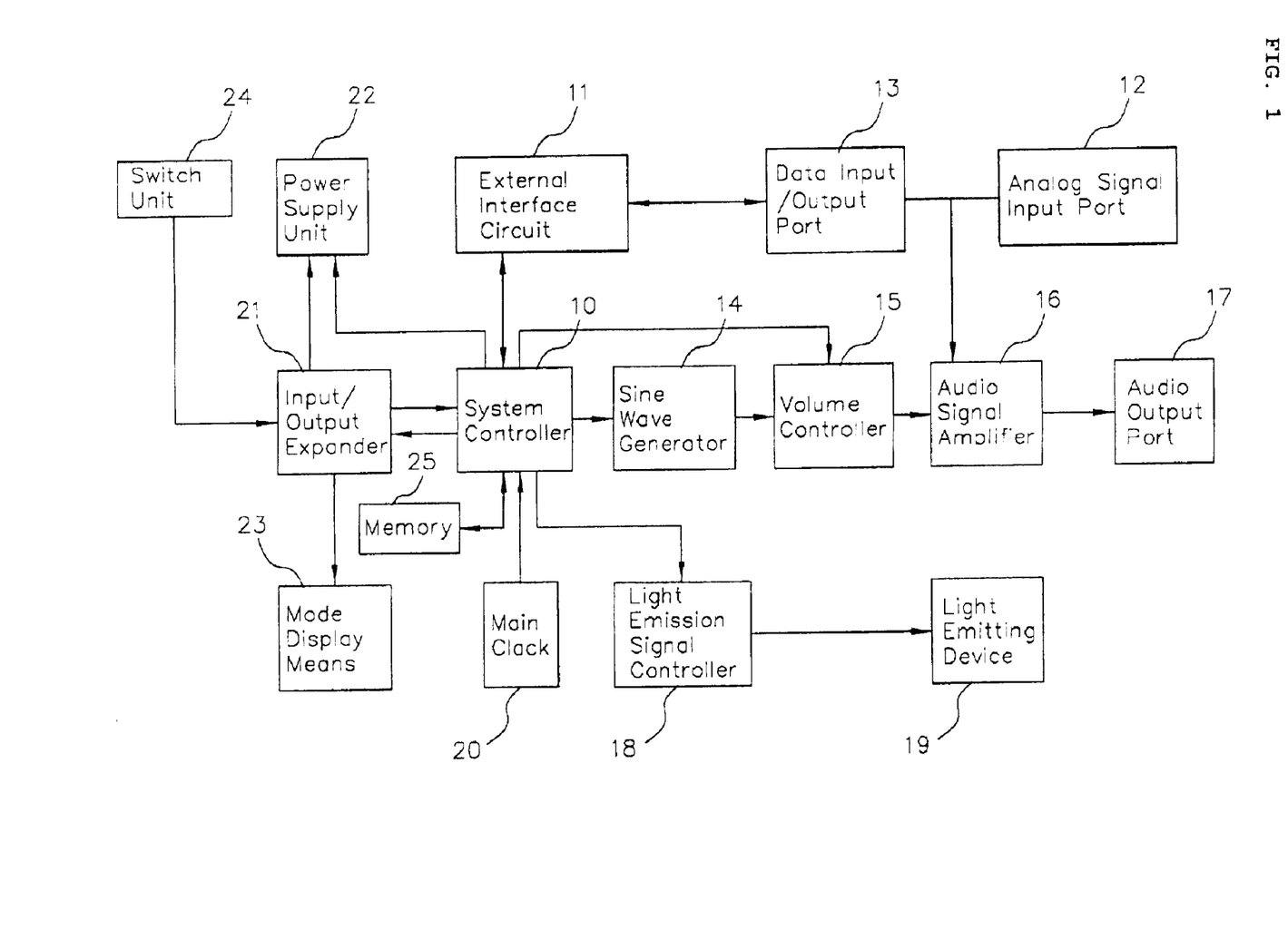
FIG. 1 is a block diagram of a first apparatus for generating brain wave-inducing signals according to a first preferred embodiment of the present invention.
Figure 2:
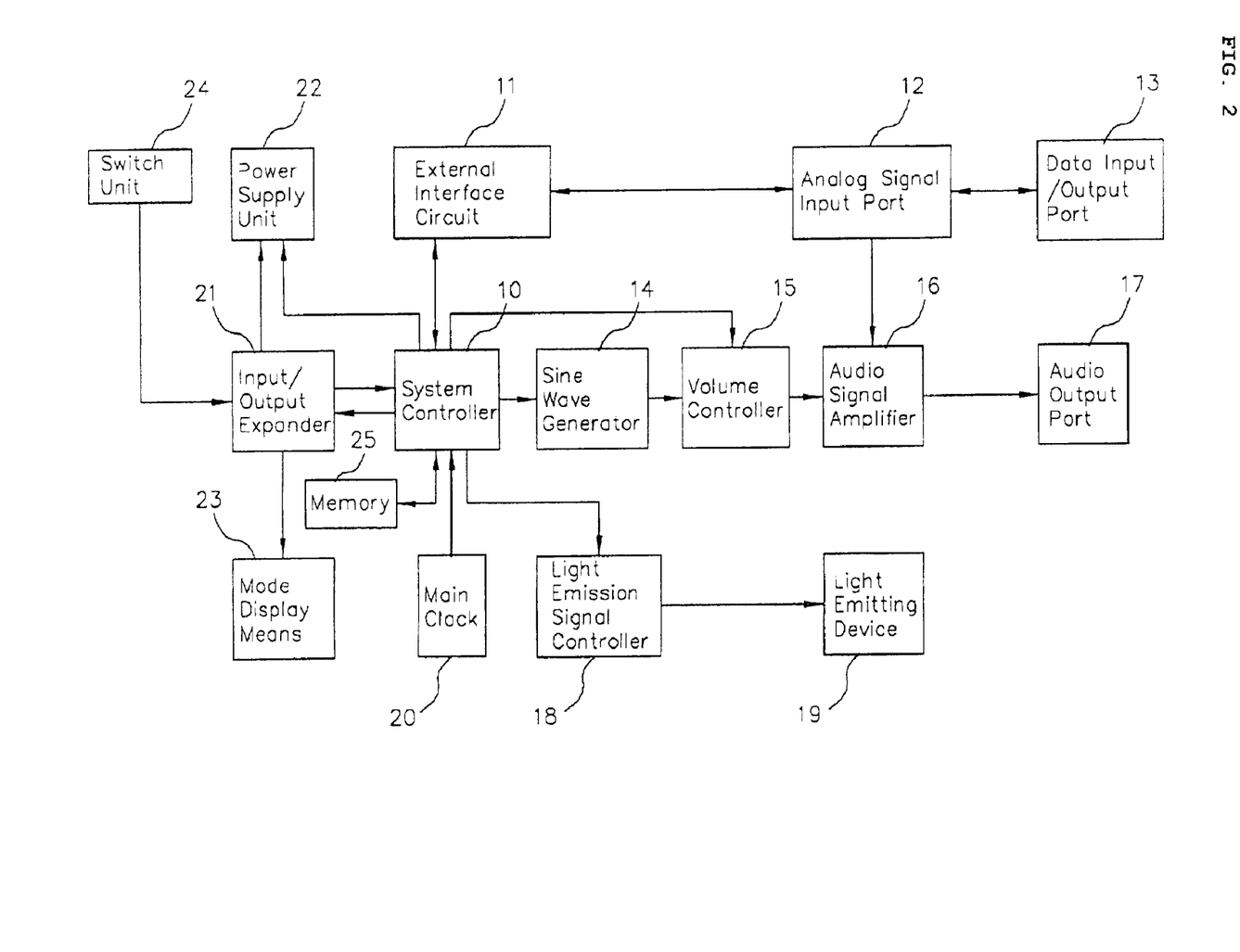
FIG. 2 is a block diagram of a second apparatus for generating brain wave-inducing signals according to a second preferred embodiment of the present invention.

FIG. 1 is a block diagram of a first apparatus for generating brain wave-inducing signals according to a first preferred embodiment of the present invention, and FIG. 2 is a block diagram of a second apparatus for generating brain wave-inducing signals according to a second preferred embodiment of this invention. The second preferred embodiment of FIG. 2 is different from that of FIG. 1 in that a single port for digital and analog signals is applied as data input/output means, and a signal separator to separate the digital and analog signals is employed.

Hereinafter, the brain wave-inducing signal generating apparatus according to the first embodiment of the present invention is described in detail, and the second embodiment thereof is described in detail only for the signal separator. In this case, the same reference numerals are used throughout the different drawings to designate the same or similar components.

The brain wave-inducing signal generating apparatus of the present invention comprises a memory unit 25, a selection switch unit 24 for various modes, a system power supply unit 22, an audio signal amplifying unit 16, a light emitting device 19, an input/output expander 21, and a mode display means 23 to display a selection mode, which are conventional components.

The selection switch unit 24 constituting the part of the brain wave-inducing signal generating apparatus comprises a power switch, a light intensity control switch, a volume control switch, a mode conversion switch, etc.

If a power supplying signal or power interrupting signal is inputted from the power switch, the system power supply unit 22 is controlled in response to a control signal of a system controller 10 through the input/output expander 21.

The quantity of emitted light can be typically controlled by adjusting the timing of a high-level signal. When a signal is inputted to the light intensity control switch, the signal is passed through the input/output expander 21, and processed by and outputted from the system controller 10 to have an intensity-controlled light emission signal.

When a signal is inputted to the volume control switch, the signal is passed through the input/output expander 21, and processed by the system controller 10. Therefore, the system controller 10 outputs a control signal for converting a brain wave-inducing signal selected through the mode conversion switch to have a predetermined intensity (volume) to the volume controller 15.

The mode conversion switch includes a brain wave selection mode and a download mode. The brain wave selection mode is a mode for selecting a desired signal of combinations of various brain wave-inducing signals stored in the memory unit 25. When a signal for selecting a specific mode is inputted, the signal is passed through the input/output expander 21, and processed by the system controller 10. Then, the system controller 10 controls brain wave-inducing signal generating units 14, 15 and 18 so as to generate a light emission signal and an audio signal.

The download mode is a mode for activating an internal program required to download a file from the outside. However, the download mode can be realized in such a way that the internal program is automatically activated immediately after power is supplied, or after a predetermined period of time elapses from the supply of power, without being additionally provided.

Operation states of the control switches which constitute the selection switch unit 24 are displayed using the mode display means 23 such as an organic light emitting device through the input/output expander 21 in response to a control signal of the system controller 10.

The system controller 10 can be typically implemented as a microcontroller, and controls the operations of the system power supply unit 22, the input/output expander 21, an external interface circuit unit 11, and the brain wave-inducing signal generating units 14, 15 and 18 which generate the audio signal and the light emission signal. Reference numeral 20 which is not described is a main clock.

A digital data input/output port 13 is used to input digital signals from an external device, or output digital signals to an external device. In this case, the external device includes a computer. Definitely, a digital signal source includes files stored in data storage media, such as a hard disc, a floppy disc, a compact disc-read only memory (CD-ROM), etc., and especially, may include files downloaded through a communication network such as the Internet.

Figure 3:
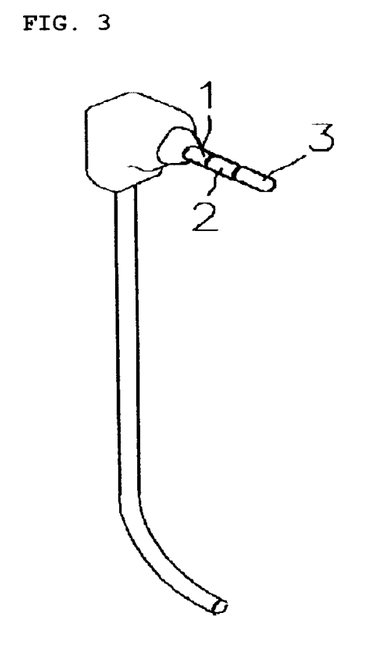
FIG. 3 is a block diagram of an external connector used in the brain wave-inducing signal generating apparatus of the present invention.

FIG. 3 is a block diagram of an external connector (for example, a mobile phone jack can be used) coupled with the data input/output port 13 according to a preferred embodiment of the present invention. The external connector is comprised of a digital signal input unit 3, a digital signal output unit 2 and a ground unit 1. For a small-sized connector used for mobile phones, the input and output units 3 and 2 and the ground unit 1 may be shorted when the connector is attached/detached to/from the data input/output port 13, so there is a risk of damages to devices. Therefore, the system controller 10 preferably controls an output signal of the data input/output port 13 to be activated after the signal input unit 3 is connected to the data input/output port 13.

Further, the present invention may include an additional input port 12 for receiving analog signals from an external device. In this case, the analog signals are transmitted to the audio signal amplifying unit 16 and outputted through an audio output port 17.

For the second embodiment in which a data input/output port is used as a single port for inputting/outputting digital signals and inputting analog signals, the connector may be comprised of a ground unit 1, a right analog signal input/digital signal input unit 3, and a left analog signal input/digital signal output unit 2.

The analog signals include signals outputted from output terminals of conventional sound devices such as audio components, an audio cassette tape recorder, a sound card, etc.

If the data input/output port is desired to be used as a single port, as in the case of the second embodiment of the present invention, an additional signal separating means (illustrated in FIG. 3) of FIG. 2 is required.

The signal separating means 12' is used to separate the analog signals and the digital signals inputted from the single port 13. The signal separating means uses a difference between electrical characteristics of analog and digital signals, and can be simply implemented using an electronic circuit.

Figure 4:
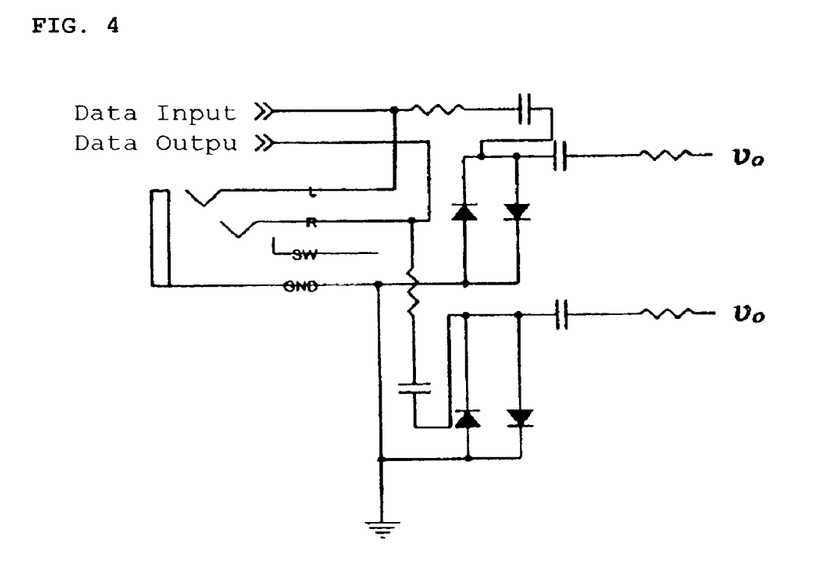
FIG. 4 is a circuit diagram of a signal separating means included in the brain wave-inducing signal generating apparatus of FIG. 2.

FIG. 4 shows the signal separating means 12' implemented as an electronic circuit according to a preferred embodiment of the present invention.

The signal separating means 12' is an analog signal input circuit unit, and preferably comprises a clipper circuit unit to capture small analog signals, a filer comprised of resistors and capacitors to eliminate undesirable noise and an input impedance protection circuit unit. The analog signals pass through the analog signal input circuit unit and are transmitted to the audio signal amplifying unit 16.

Digital signals cannot pass through the analog signal input circuit unit, so they are transmitted to the system controller 10 via the interface circuit 11.

However, it should be noted that the above embodiment of FIG. 4 is only an example for describing the present invention sufficiently. Therefore, those skilled in the art will appreciate that modifications through various electronic devices and their combinations are possible, without departing from the scope and spirit of the invention.

The digital signals include an arbitrary signal inputted from an external device, and preferably include information (hereinafter, referred to as "signal information") for generating brain wave-inducing signals. In this case, the signal information preferably includes frequency information, signal intensity (brightness) information, etc. for the light emission signal, and includes frequency information, signal intensity (volume) information and pitch information, etc. for the audio signal.

The light emission signal and the audio signal can be each controlled to be synchronized in their left and right signals or not synchronized. Further, the light emission signal and the audio signal can be controlled to be synchronized with each other or not synchronized.

The signal information has preferably a form of a file, which can be provided from a hard disc, a floppy disc, a CD-ROM, or a specific Web server through a communication network including the Internet, etc. The user can use the signal information by downloading the signal information from a computer (including a client) and storing it in the memory 25.

The signal information can have various combinations of frequencies, intensities and pitches according to kinds of brain waves to be induced. This variety reflects the fact that brain wave characteristics and degrees of responses to the brain wave-inducing signals are different according to persons who desire to use the signal information. Therefore, the user selects a signal suitable for him, thus executing induction of brain waves under an optimal condition.

The external interface circuit 11 is used to interface digital signals inputted from the digital data input/output port 13 with signals of the system controller 10. The external interface circuit 11 is not limited in its type, and can be realized by a chip (for example, MAX3221) into which a conventional circuit is integrated.

The brain wave signal generating units 14, 15 and 18 include an audio signal generating unit and the light emission signal controller.

The audio signal generating unit is not especially limited; however, it preferably includes the sine wave generating unit 14 to generate a sine wave from digital signals inputted from the system controller 10 and the volume controller 15 to output the sine wave to have a predetermined volume under the control of the system controller 10.

In this case, the audio signal is a sound signal which is represented by periodic pulses for inducing specific brain waves, wherein the sound signal has a predetermined frequency, and is adjusted in its intensity. Such an audio signal will be described later.

Figure 5A:
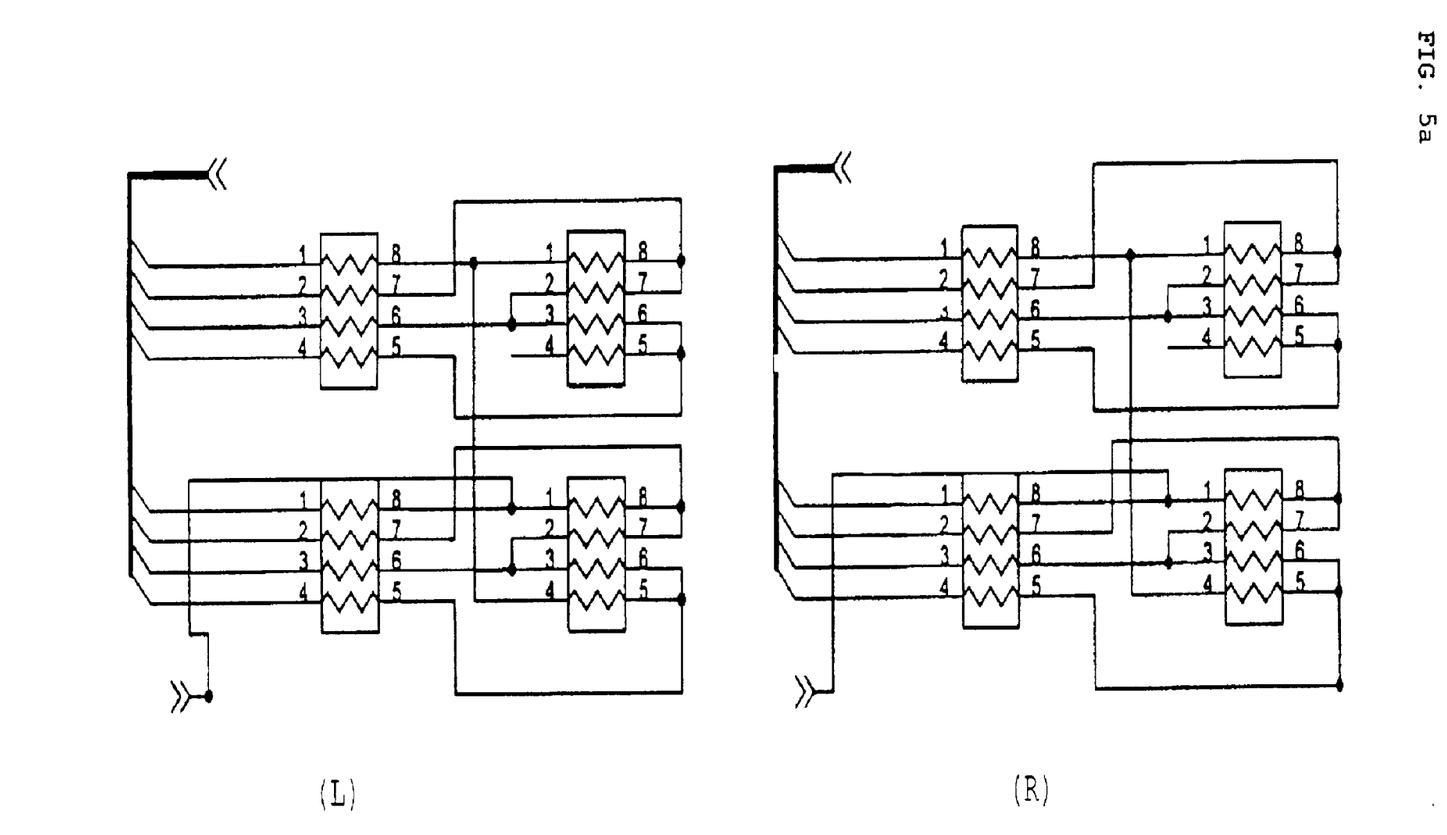
FIGS. 5a and 5b are circuit diagrams of first and second sine wave generating circuits according to preferred embodiments of the present invention, respectively, wherein L indicates left and R indicates right.
Figure 5B:
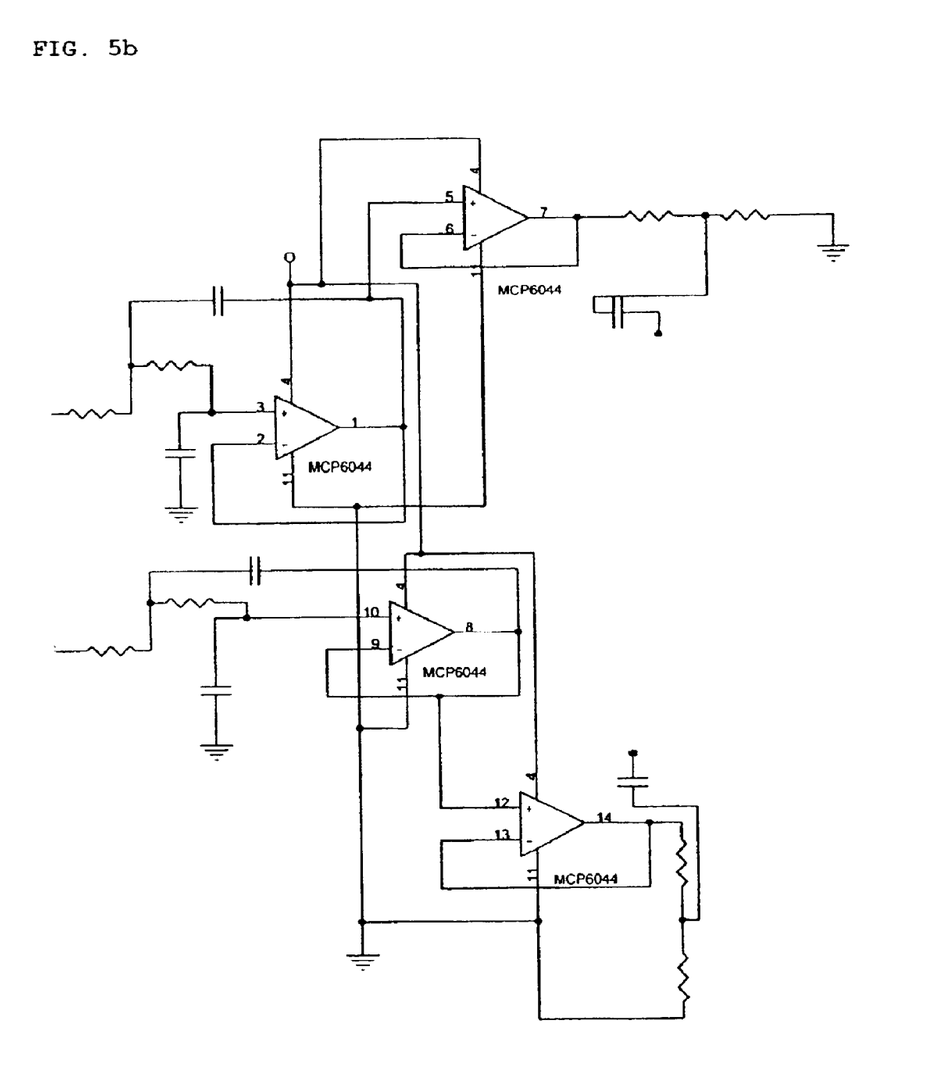
Figure 6A:
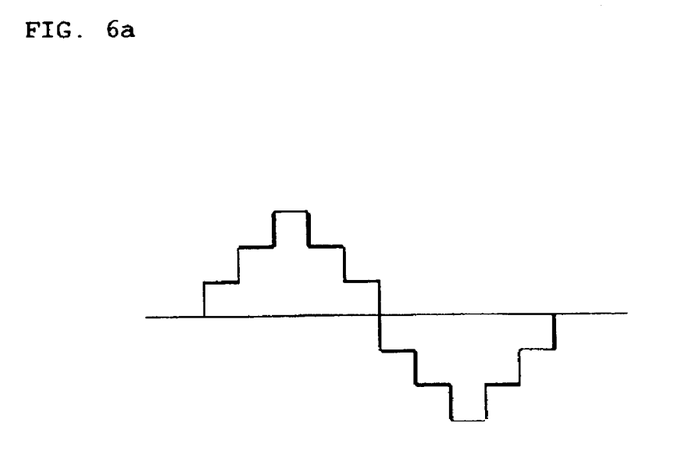
FIGS. 6a and 6b are graphs showing a first sine wave and a filtered second sine wave, respectively.
Figure 6B:
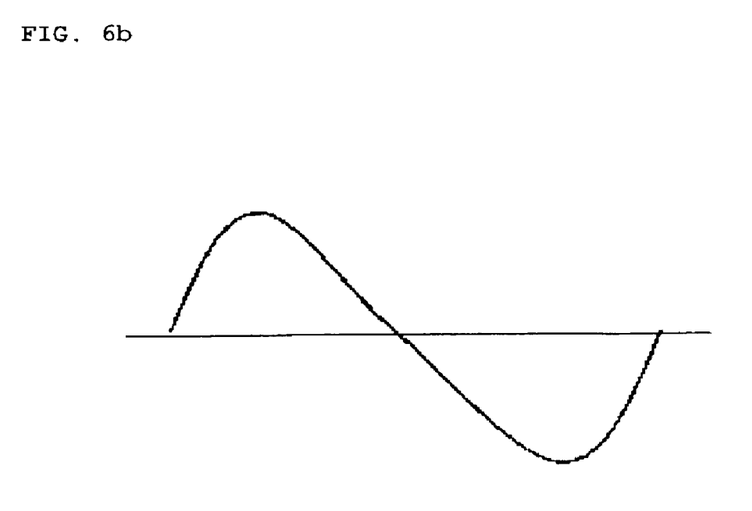

The since wave generating unit 14 can be implemented by circuits shown in detain in FIGS. 5a and 5b. According to the circuits, a first sine wave with a step shape of FIG. 6a is extracted from digital signals by a converter circuit of FIG. 5a. The stepped sine wave is transmitted to a filter circuit of FIG. 5b, such as a Tchebychev filter, thus obtaining a perfect second sine wave of FIG. 6b. However, the circuits of FIGS. 5a and 5b are only examples for appreciation of the present invention, and the sine wave generating unit 14 is not limited to the circuits of FIGS. 5a and 5b.

Then, the sine wave signal generated by the sine wave generating unit 14 is inputted to the volume controller 15. The volume controller 15 generates an audio signal of a predetermined volume from the sine wave signal in response to a control signal of the system controller 10. It is possible to realize the control signal for volume control to be directly inputted by the switch 24, as well as the system controller 10. However, for such a case, additional hardware may be required.

Figure 7:
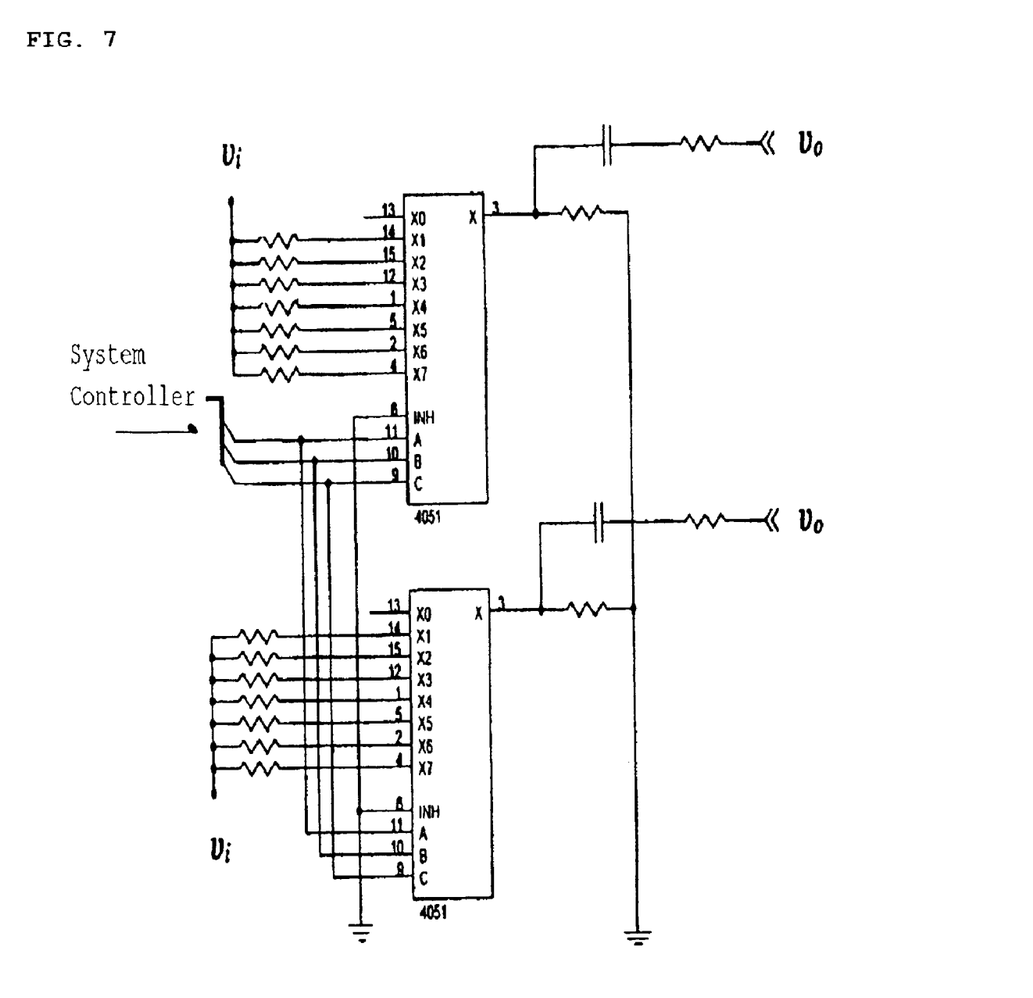
FIG. 7 is a circuit diagram of a volume controller according to a preferred embodiment of the present invention.

FIG. 7 is a detailed circuit diagram of a preferred embodiment of the volume controller 15. The volume controller 15 has a signal converting circuit to convert the sine wave signal generated by the sine wave generating unit 14 into an audio signal with a predetermined intensity in response to the control signal of the system controller 10.

The audio signal outputted from the volume controller 15 is amplified to have an audible intensity by the audio signal amplifying unit 16, and the amplified audio signal is outputted through the audio output port 17.

Figure 8:
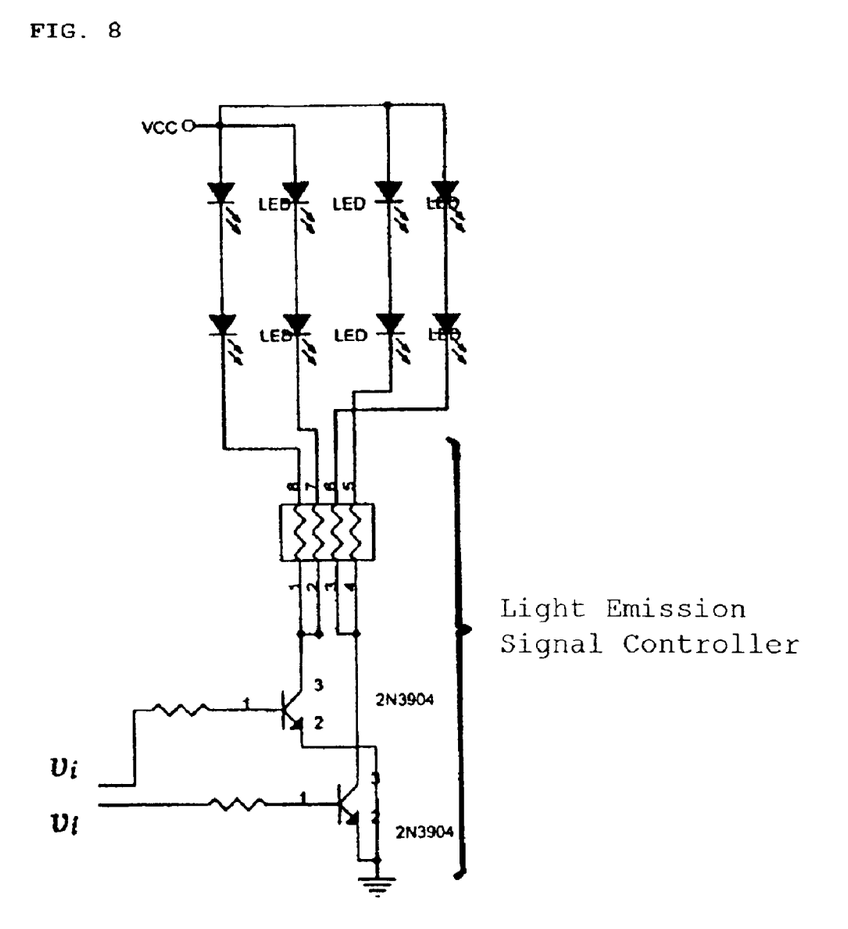
FIG. 8 is a circuit diagram of a light emission signal controller according to a preferred embodiment of the present invention.

Further, the light emission signal controller 18 constituting the brain wave-inducing signal generating unit outputs a light emission signal with a predetermined frequency, generated by the system controller 10 as a signal recognizable by the light emitting device 19 using a detailed circuit shown in FIG. 8.

In this case, the light emission signal includes an arbitrary signal having a predetermined frequency and generating periodic visual changes.

Preferably, the light emission signal includes periodic on and off states of an organic light emitting device, and can be adjusted in its brightness using the timing of high and low signals. The light emission signal is described in detail as follows.

Each of the audio signal and the light emission signal includes independently one of frequencies of 8 to 13 Hz for inducing the alpha waves generated under stable conditions a normal person, such as during paying attention, simple learning and meditation, frequencies of 14 to 30 Hz for inducing the beta waves generated in states of increased brain activity, or when under of strain, frequencies of 4 to 7 Hz for inducing the theta waves generated during light sleep, or frequencies of lower than 4 Hz for inducing the delta waves generated during deep sleep and independently generated by an external cortex itself. Alternatively, each of the audio signal and the light emission signal may include combined signals of two or more frequencies among the above frequency groups.

Figure 9:
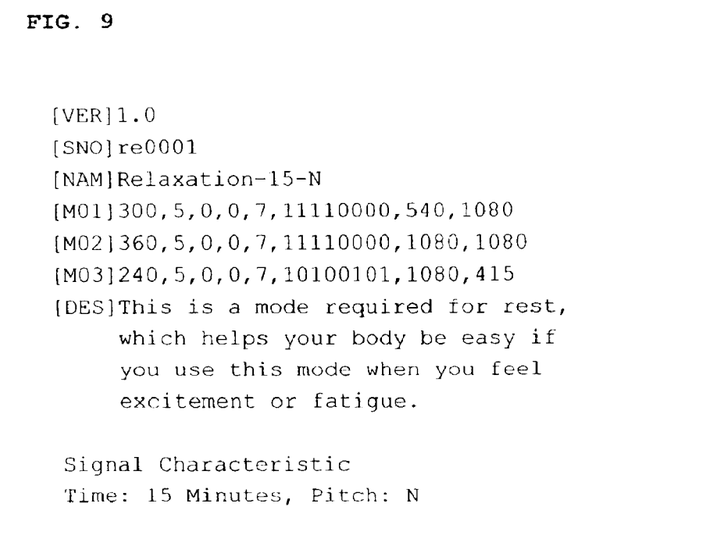
FIG. 9 is a view showing an example of a brain wave-inducing signal file of the present invention.
Figure 10:
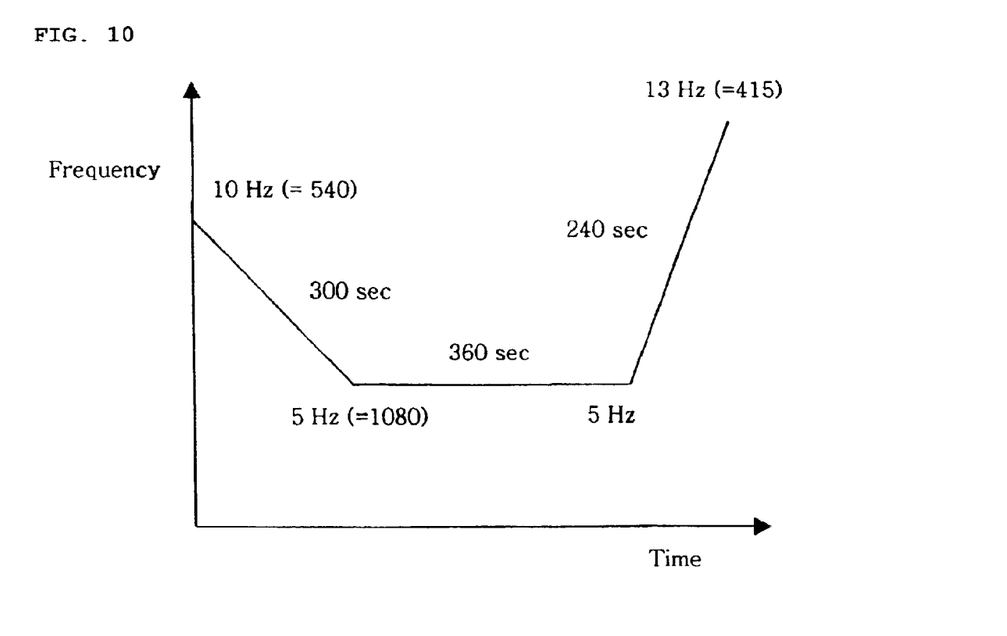
FIG. 10 is a graph showing an example of a brain wave-inducing signal obtained from the brain wave-inducing signal file of FIG. 9.

FIGS. 9 and 10 show an example of a brain wave-inducing signal file practically stored in the memory. Those skilled in the art will appreciate that file formats to be described later can be easily modified and revised from descriptions of the present invention. Hereinafter, the brain wave-inducing signal file is described in detail with reference to FIG. 9.

The file contains its version information VER, a serial number SNO, a name of a brain wave-inducing signal NAM, a description of a brain wave-inducing signal DES, and segment information MO1, MO2, MO3, etc.

The exemplary segment information contains information on a time of a single segment, a duty cycle representing a ratio (indicated by 1 to 9) of the first half of one cycle to one cycle, light intensity (indicated by integer values of −3 to 3), a volume representing sound intensity (indicated by integer values of −3 to 3), a sine table number for determining pitch (indicated by integer values of 0 to 14), a phase for determining on/off states of sound and light during the first half and the second half of one cycle, start frequency information which is frequency information at the start of a segment, and end frequency information which is frequency information at the end of a segment.

If a value of the duty cycle is 4, it means that the first half of a cycle occupies 40% of the cycle. Further, provided that a default is 0, if each value of the light intensity and the volume is negative, it means that the light intensity and the volume decrease by stages, while if each value of the light intensity and the volume is positive, it means that the light intensity and the volume increase by stages.

The frequency (unit: KHz) of the pitch based on a sine table can be set to 0:163.64, 1:174.19, 2:192.86, 3:216.00, 4:245.45, 5:257.14, 6:300.00, 7:337.50, 8:360.00, 9:385.71, 10:415.38, 11:450.00, 12:490.91, 13:540.00, 14:600.00, etc.

The phase is indicated by a 8-bit signal, in which the first 4 bits represent the first half of a cycle, and the last 4 bits represent the second half of the cycle. Each of the 4 bits represents left light, right light, left sound, and right sound in turn. For a segment 1, the phase of the segment 1 is represented by 11110000, so left and right sounds and lights are turned on during the first half of the cycle, while they are turned off during the second half of the cycle. Further, for a segment 3, the phase of the segment 3 is represented by 10100101, so only left light and left sound are turned on during the first half of the cycle, while only right light and right sound are turned on during the second half of the cycle.

The start and end frequencies of the segment can be represented by integer values of 135 to about 20,000. For example, if the system controller 10 sets a cycle for calculating a brain wave-inducing signal to 5400 Hz, both the start and end frequencies for generating a brain wave-inducing signal of 10 Hz, which is an alpha wave, would be 540 (5400/10) Hz.

Figure 11:
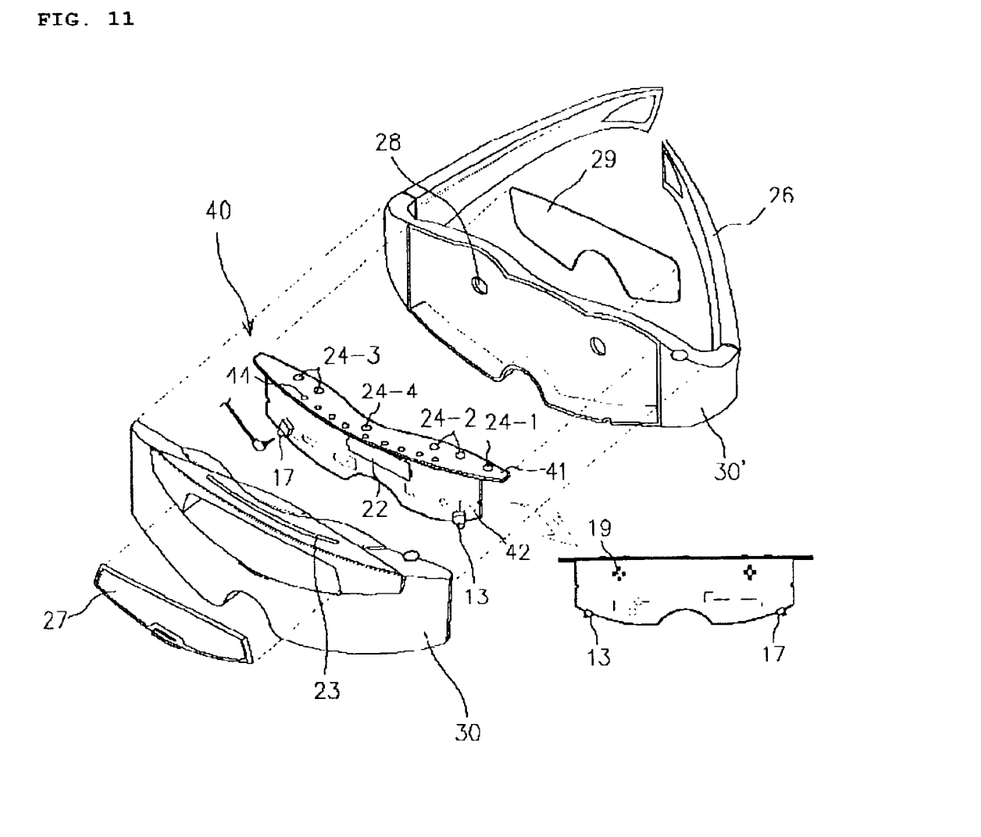
FIG. 11 is an exploded perspective view of an optical glasses unit in which the brain wave-inducing signal generating apparatus of the present invention is practically implemented.

FIG. 11 shows an embodiment of the brain wave-inducing signal generating apparatus in which the present invention is practically implemented.

The brain wave-inducing signal generating apparatus has a construction in which an optical glasses and a main body are integrated into one. The brain wave-inducing signal generating apparatus comprises a casing having function selection buttons, a control circuit board 40 arranged at a predetermined position within the casing and provided with a circuit to control an output of a brain wave-inducing signal, a data input/output unit 13 to exchange data with an external device, a brain wave-inducing signal output unit comprised of light emitting devices 19 and an audio signal output unit 17 which are electrically connected to the control circuit board 40, and a power supply unit 22.

Hereinafter, the preferred embodiment of the present invention is described in detail with reference to the above construction.

The casing of the brain wave-inducing signal generating apparatus is separated into a front casing 30 and a back casing 30'.

The front casing 30 has a covering unit 27 covered with an opening formed in the front surface of the front casing 30 so as to allow the opening to accommodate a battery. On the top surface of the front casing 30, buttons each with a predetermined shape are attached, wherein the buttons respectively correspond to a power switch 24-1, a light intensity control switch 24-2, a volume control switch 24-3 and a mode conversion switch 24-4 included in a function selection switch unit. Further, on the top surface of the front casing 30, a mode display window 23 to display a current mode state is arranged.

Arms 26 foldably formed to be supported on ears are disposed at both ends of the back casing 30'. Further, two openings 28 are respectively formed in left and right portions around the center of the back casing 30'. Further, on the back surface of the back casing 30', typical protective glasses 29 for protecting the eyes of a user are attached.

The small-sized circuit board 40 in which the apparatus of FIG. 2 is implemented is comprised of an upper board 41 and a lower board 42 perpendicular thereto. There are formed on the upper board 41 the power switch 24-1, the light intensity control switch 24-2, the volume control switch 24-3 and the mode conversion switch 24-4 included in the function selection switch unit 24, and a light emitting diode (LED) unit 44. The power supply unit 22 is arranged on the front surface of the lower board 42. Further, a control circuit comprised of various devices for controlling operations of the brain wave-inducing signal generating apparatus is arranged over the front and back surfaces of the lower board 42.

One or more LEDs 19, which are light emitting devices, are prepared as means for outputting the brain wave-inducing signal. Left-right sets of LEDs are arranged on the back surface of the lower board 42. Further, an earphone connection port 17 which is an audio output port, and a digital data input/output port 13 to provide interface with the external device are disposed on the lower board 42.

The brain wave-inducing signal generating apparatus of the above embodiment has a plurality of brain wave modes, which can be classified into the following modes.

A first mode M1 is a concentration mode, in which brain waves for improving concentration under unstable conditions are induced.

A second mode M2 is a learning mode, in which brain waves for maintaining concentration and activating functions of a brain to improve memory are induced.

A third mode M3 is a language study mode, in which brain waves for maintaining concentration are outputted together with audio output signals of teaching materials for language study, received from an external device.

A fourth mode M4 is a rest mode, in which brain waves for calming human emotions and reducing a sense of fatigue are induced.

A fifth mode M5 is a meditation mode, in which brain waves for calming human emotions and providing feelings of purification are induced.

A sixth mode M6 is a vitality mode, in which brain waves for reducing tension and stress are induced.

A seventh mode M7 is a sleeping mode, in which brain waves for allowing a user to sleep deeply are induced.

The above brain waves M1 to M7 are only exemplary modes, which can be easily modified and revised by those skilled in the art.

Referring to the above segment information, light stimulation is generated by four LEDs 19 arranged in each of left and right parts, and is controlled to be classified in its brightness into seven steps by the user's manipulation of the switch 24-2. The system controller 10 controls brightness and on/off frequencies of light according to characteristics of the brain wave-inducing signal, thus enabling light stimulation with a specific frequency (for example, red color) to be outputted.

Sound stimulation is generated by left and right earphones, and is controlled to be classified into seven steps by the user's manipulation of the switch 24-3 The system controller 10 generates a sound signal (audio signal) with a specific frequency using a digital method according to characteristics of the brain wave-inducing signal. The sound signal is outputted to the earphone through the sine wave generating unit 14, the volume controller 15 and the audio signal amplifying unit 16. In this case, pitch is determined according to characteristics of the sound signal generated by the system controller 10, and is classified into fifteen steps and outputted. The pitch is predetermined as one of characteristics of the brain wave-inducing signal, and provided variably. Further, the pitch is selected to correspond to the user's preference.

Figure 12:
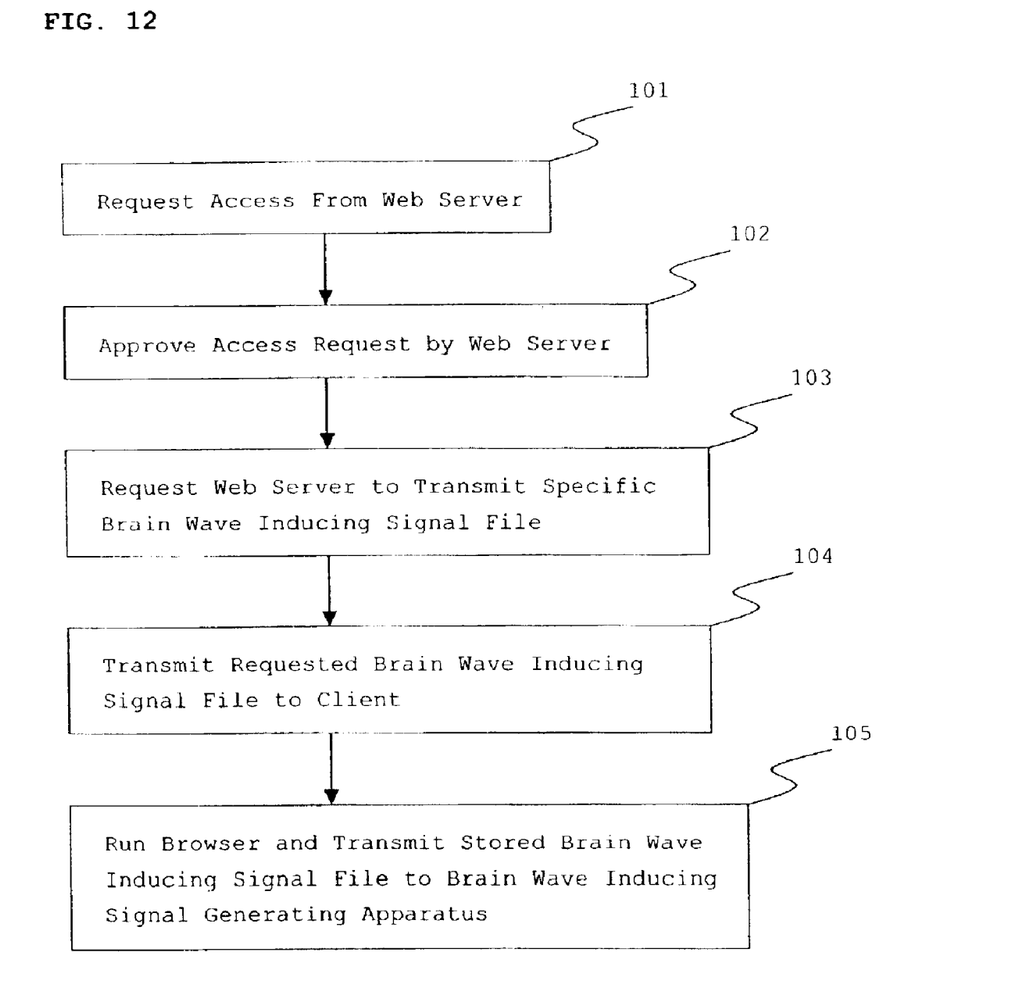
FIG. 12 is a flowchart of a process of downloading a brain wave-inducing signal file from a Web server.

Further, the present invention provides a method of downloading a brain wave-inducing signal file of a desired mode from a Web server on a network. Such a download method is depicted in FIG. 12.

That is, the download method of the present invention comprises the steps of:

(a) a client requesting access from the Web server at step 101, (b) the Web server approving the access request from the client at step 102, (c) the client requesting the Web server to transmit a specific brain wave-inducing signal file at step 103, (d) the Web server transmitting the requested brain wave-inducing signal file to the client at step 104, and (e) running a browser of the client, and transmitting a stored brain wave-inducing signal file to the brain wave-inducing signal generating apparatus at step 105.

In the above process, communication between the client and the Web server can be achieved through a conventional communication protocol, and includes a typical access process and a download process. Therefore, the user requests the access from the Web server by entering the URL of the Web server. Further, the Web server approves the access of the client thereto after performing a user authentication procedure according to cases.

Figure 13:
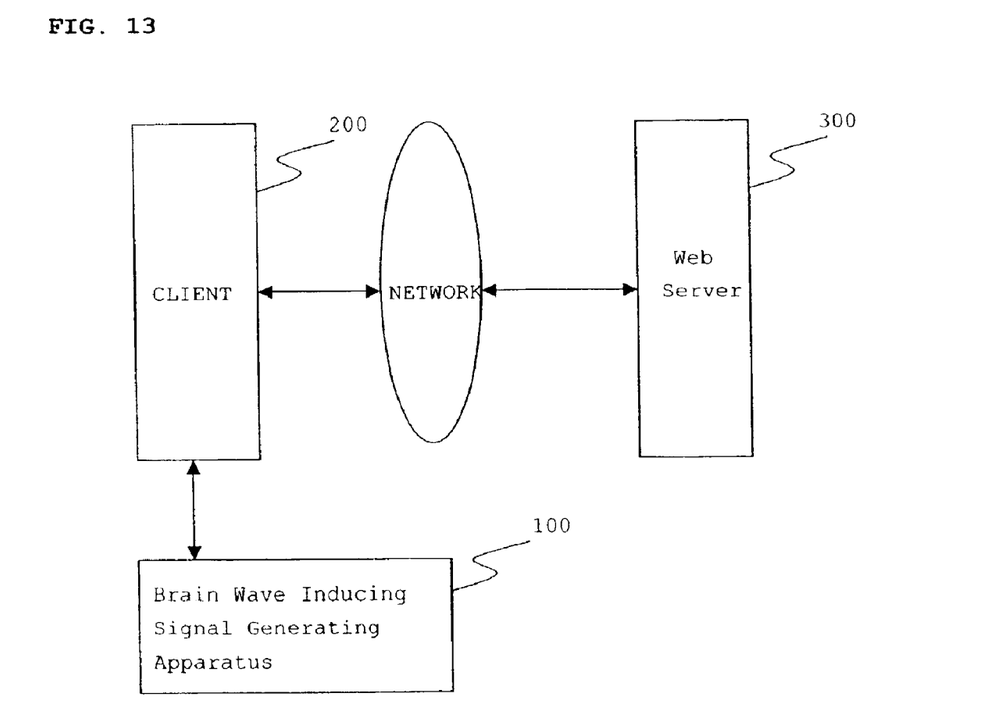
FIG. 13 is a block diagram of a network system according to the present invention.

As shown in FIG. 13, a Web server 300 stores a variety of brain wave-inducing signal files having forms shown in FIG. 9 in a database (DB), and provides a variety of brain wave-inducing signal files to an authenticated user through a home page of the Web server 300.

The brain wave-inducing signal generating apparatus 100 has a program required to store a desired file in its internal memory after the client 200 accesses the Web server 300 and downloads the desired file.

When the user accesses the Web server 300 and desires to download a brain wave-inducing signal file of a desired mode, the user converts the mode conversion switch of the brain wave-inducing signal generating apparatus into the download mode, and then executes the program, thus completing preparation for the download. Then, the user downloads a desired brain wave-inducing signal file by accessing a corresponding Web site, runs the browser of the client 200, communicating with the brain wave-inducing signal generating apparatus 100, and stores the downloaded file in the memory.

In the preferred embodiment of the present invention, a jack with a diameter of 2.5 mm is used as an embodied physical means for communicating with the computer in which the brain wave-inducing signal generating apparatus 100 and the client 200 are installed. Further, the jack is a port connected to a serial port of the computer so as to interface with the computer. As described above, the port can also be provided as an input port for allowing a brain wave-inducing signal input port and an audio output terminal of another device to be combined and used, such as for use in the language study mode, as well as the input port for downloading the brain wave-inducing signal from the client 200.

As described above, the present invention provides an apparatus for generating brain wave-inducing signals and network system including the same, which can be miniaturized by integrating several parts into one through the combination of simple hardware with software, and can receive analog and digital signals from an external device. Further, the present invention is advantageous in that it can increase the variety of signal selection by downloading a suitable brain wave-inducing signal according to characteristics of users from an external communication network.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for generating brain wave-inducing signals, comprising:

a system controller;

a data input/output port for receiving digital signals from an external device which are coupled to the system controller including information for generating brain wave-inducing signals; and a brain wave-inducing signal generating unit for generating brain wave-inducing signals including an audio signal and a light emission signal under the control of the system controller and wherein the audio signal and the light emission signal are generated by the brain wave-inducting signal generating unit from information downloaded from an information source through a communication network.

2. The brain wave-inducing signal generating apparatus according to claim 1, further comprising an analog signal input port.

3. The brain wave-inducing signal generating apparatus according to claim 1, wherein the brain wave-inducing signal generating unit comprises an audio signal generating unit and a light emission signal generating unit.

4. The brain wave-inducing signal generating apparatus according to claim 3, wherein the audio signal generating unit comprises a sine wave generating unit for generating a sine wave from digital signals inputted from the system controller, and a volume controller for outputting the sine wave to have a predetermined volume under the control of the system controller.

5. The brain-wave inducing signal generating apparatus according to claim 1, wherein the brain wave-inducing signals are signals for inducing at least one type of brain waves selected from alpha, beta, theta and delta waves.

6. The brain wave-inducing signal generating apparatus according to claim 1, wherein the information for generating the audio signal and the light emission signal is provided from files stored in a hard disc, a floppy disc, or a compact disc-read only memory (CD-ROM).

7. An apparatus for generating brain wave-inducing signals, comprising:
   a system controller;
   a data input/output port comprised of a single port for receiving analog and digital signals from the outside which are coupled to the system controller;
   signal separating means for separating the analog signals and digital signals; and
   a brain wave-inducing signal generating unit for generating an audio signal and a light emission signal under the control of the system controller.

8. The brain wave-inducing signal generating apparatus according to claim 7, wherein the brain wave-inducing signal generating unit comprises an audio signal generating unit and a light emission signal generating unit.

9. The brain wave-inducing signal generating apparatus according to claim 8, wherein the audio signal generating unit comprises a sine wave generating unit for generating a sine wave from digital signals inputted from the system controller, and a volume controller for outputting the sine wave to have a predetermined volume under the control of the system controller.

10. The brain wave-inducing signal generating apparatus according to claim 7, wherein the brain wave-inducing signal is a signal for inducing at least one type of brain waves selected from alpha, beta, theta and delta waves.

11. The brain wave-inducing signal generating apparatus according to claim 7, wherein the audio signal and the light emission signal are generated from files stored in a hard disc, a floppy disc, or a compact disc-read only memory (CD-ROM).

12. The brain wave-inducing signal generating apparatus according to claim 7, wherein the audio signal and the light emission signal are generated by the brain wave-inducing signal generating unit from information downloaded from an information source through a communication network; and wherein
   the brain wave-inducing output unit generates light and sound.

13. The brain wave-inducing signal generating apparatus according to claim 12, wherein the brain wave-inducing signal generating unit comprises an audio signal generating unit and a light emission signal generating unit.

14. The brain wave-inducing signal generating apparatus according to claim 13, wherein the audio signal generating unit comprises a sine wave generating unit for generating a sine wave from digital signals inputted from the system controller, and a volume controller for outputting the sine wave to have a predetermined volume under the control of the system controller.

15. The brain wave-inducing signal generating apparatus according to claim 12, wherein the brain wave-inducing signal is a signal for inducing at least one type of brain waves selected from alpha, beta, theta and delta waves.

16. The brain wave-inducing signal generating apparatus according to claim 12, wherein the information for generating the audio signal and the light emission signal is provided from files stored in a hard disc, a floppy disc, or a compact disc-read only memory (CD-ROM).

17. An apparatus for generating brain wave-inducing signals, comprising:
   a casing having at least one function selection button;
   a control circuit board arranged at a predetermined position within the casing and provided with a circuit for controlling an output of a brain wave-inducing signal;
   a data input/output unit for exchanging data with an external device;
   a brain wave-inducing signal output unit comprised of at least one light emitting device and an audio signal output port which are electrically connected to the control circuit board; and
   a power supply unit; and wherein
   the brain wave-inducing signal output unit generates light and sound from information downloaded from an information source through a communication network.

18. A method of downloading a brain wave-inducing signal file of a desired mode from a Web server on a network, comprising the steps of:
   a client requesting access from the Web server;
   the Web server approving the access request from the client;
   the client requesting the Web server to transmit a specific brain wave-inducing signal file;
   the Web server transmitting the requested brain wave-inducing signal file to the client; and
   running a browser installed in the client, and transmitting a stored brain wave-inducing signal file to a brain wave-inducing signal generating apparatus.

19. A network system, comprising:
   a brain wave-inducing signal generating apparatus comprised of a system controller, a data input/output port for receiving digital signals from an external device, and a brain wave-inducing signal generating unit for generating an audio signal and a light emission signal under the control of the system controller;
   a client for communicating with the brain wave-inducing, signal generating apparatus through a predetermined communication program; and
   a Web server mutually connected to the client on a network and provided with a database in which brain wave-inducing signal files are stored.

20. The network system according to claim 19, wherein the brain wave-inducing signal generating unit comprises an audio signal generating unit and a light emission signal generating unit.

21. The network system according to claim 20, wherein the audio signal generating unit comprises a sine wave generating unit for generating a sine wave from digital signals inputted from the system controller, and a volume controller for outputting the sine wave to have a predetermined volume under the control of the system controller.

22. The network system according to claim 19, wherein the brain wave-inducing system is a signal for inducing at least one type of brain waves selected from alpha, beta, theta and delta waves.

23. A network system, comprising:

a brain wave-inducing signal generating apparatus comprised of a system controller, a data input/output port comprised of a single port for receiving analog and digital signals from the outside, signal separating means for separating the analog signals and the digital signals, and a brain wave-inducing signal generating unit for generating an audio signal and a light emission signal under the control of the system controller;

a client for communicating with the brain wave-inducing signal generating apparatus through a communication program; and a Web server mutually connected to the client on a network and provided with a database in which a variety of brain wave-inducing signal files are stored.

24. The network system according to claim 23, wherein the brain wave-inducing signal generating unit comprises an audio signal generating unit and a light emission signal generating unit.

25. The network system according to claim 24, wherein the audio signal generating unit comprises a sine wave generating unit for generating a sine wave from digital signals inputted from the system controller, and a volume controller for outputting the sine wave to have a predetermined volume under the control of the system controller.

26. The network system according to claim 23, wherein the brain wave-inducing signal is a signal for inducing at least one type of brain waves selected from alpha, beta, theta and delta waves.

* * * * *